United States Patent [19]

Lorenz et al.

[11] Patent Number: 4,769,013
[45] Date of Patent: Sep. 6, 1988

[54] BIO-EFFECTING MEDICAL MATERIAL AND DEVICE

[75] Inventors: Donald H. Lorenz, Basking Ridge; Walter S. Creasy, Bridgewater, both of N.J.

[73] Assignee: Hydromer, Inc., Whitehouse, N.J.

[21] Appl. No.: 870,452

[22] Filed: Jun. 4, 1986

Related U.S. Application Data

[63] Continuation-in-part of Ser. No. 416,906, Sep. 13, 1982, abandoned.

[51] Int. Cl.⁴ .......................................... A61M 5/325
[52] U.S. Cl. .................................. 604/265; 128/156; 128/157; 424/80; 106/18.24
[58] Field of Search .............. 106/18.24, 18.25, 18.35; 128/132 R, 157, 156; 424/80; 521/54, 159; 604/265, 308, 359, 360, 364

[56] References Cited

U.S. PATENT DOCUMENTS

| | | | |
|---|---|---|---|
| 2,706,701 | 4/1955 | Beller et al. | 167/70 |
| 2,739,922 | 3/1956 | Shelanski | 167/70 |
| 3,136,755 | 6/1964 | Grosser et al. | 260/239.3 |
| 3,216,579 | 11/1965 | Shelanski et al. | 210/501 |
| 3,235,446 | 2/1966 | Shelanski et al. | 167/17 |
| 3,401,005 | 9/1968 | Katz | 424/404 |
| 3,882,868 | 5/1975 | Tundermann | 128/260 |
| 3,898,326 | 8/1975 | Cantor et al. | 424/80 |
| 4,010,259 | 3/1977 | Johansson | 424/150 |
| 4,017,407 | 4/1977 | Cantor et al. | 252/106 |
| 4,094,967 | 6/1978 | Gilbert | 424/150 |
| 4,100,309 | 7/1978 | Micklus et al. | 427/2 |
| 4,113,851 | 9/1978 | LeVeen et al. | 128/156 |
| 4,119,094 | 10/1978 | Micklus et al. | 128/132 R |
| 4,137,200 | 1/1979 | Wood et al. | 521/159 |
| 4,160,076 | 7/1979 | Guthrie et al. | 521/159 |
| 4,217,254 | 8/1980 | Legue | 260/3.3 |
| 4,254,239 | 3/1981 | Straub et al. | 525/123 |
| 4,381,380 | 4/1983 | LeVeen et al. | 525/452 |
| 4,550,126 | 10/1985 | Lorenz | 521/159 |

FOREIGN PATENT DOCUMENTS

| | | |
|---|---|---|
| 2557607 | 8/1976 | Fed. Rep. of Germany . |
| 2718385 | 2/1978 | Fed. Rep. of Germany ........ 424/80 |
| 824215 | 11/1959 | United Kingdom . |

OTHER PUBLICATIONS

Literature Reference: Block, "Disinfection, Sterilization, and Preservation," 2d. Ed. (1977).

Primary Examiner—Richard J. Apley
Assistant Examiner—Paul Prebilic
Attorney, Agent, or Firm—Hoffmann & Baron

[57] ABSTRACT

A medical material comprising a polyurethane complexed with polyvinylpyrrolidone and a bio-effecting agent, such as an anti-bacterial agent, complexed with the polyvinylpyrrolidone. The material is used per se as, for example a foam, and as a coating for medical devices such as, for example, catheters and wound drainage tubes.

18 Claims, 1 Drawing Sheet

BIO-EFFECTING MEDICAL MATERIAL AND DEVICE

This application is a continuation-in-part of Ser. No. 416,906 filed on Sept. 13, 1982, now abandoned.

BACKGROUND OF THE INVENTION

This invention is in the field of medical materials and devices.

It is known to react polyvinylpyrrolidone (N-vinyl-2-pyrrolidone) with an isocyanate prepolymer and cure the reaction product to form polyvinylpyrrolidone bonded to a polyurethane to form, for example, coatings having a very low coefficient of friction when wetted with an aqueous solution. Reference may be had to U.S. Pat. Nos. 4,100,309 and 4,119,094 which are incorporated herein by reference. Such material does not dissolve when exposed to water or body fluids. It is also known to form complexes of iodine with polyvinylpyrrolidone (see U.S. Pat. Nos. 2,739,992 and 2,706,701). This material is water-soluble and would be washed away by body fluids.

In U.S. Pat. No. 3,235,446 to Shelanski a polyurethane foam or film is disclosed which is complexed with iodine for release thereof in water. There is no indication in the Shelanski '446 disclosure to provide a polyurethane-polyvinylpyrrolidone interpolymer and the Shelanski product suffers a drawback of releasing elemental iodine which is undesirable because of its irritating effect on the skin. U.S. Pat. No. 3,216,579 to Shelanski, et al. discloses a water-insoluble form of polyvinylpyrrolidone adsorbed on a granular synthetic calcium silicate. There is no suggestion by Shelanski, et al. to form a polyurethane-polyvinylpyrrolidone interpolymer for use as a medical material, e.g., film or foam.

German Offlegungsschrift No. 25 57 607 to Blank, et al. discloses a polymer containing 20–100 wt. % vinylpyrrolidone and 0–80 wt. % of other monomer units, which can be hydrophilic monomer units such as acrylic acid, methacrylic acid, itaconic acid and/or hydroxyethyl methacrylate, or hydrophobic monomer units such as alkyl acrylate and/or methacrylate. Adducts of iodine can be formed by contacting the polymer with iodine in the liquid phase at room temperature. There is no indication by Blank, et al. to use a polyvinylpyrrolidone polymer in combination with a second polymer such as a polyurethane combined or complexed as an interpolymer.

In accordance with this invention an anti-bacterial agent which for some applications is also an anti-fungal agent such as iodine is complexed with polyvinylpyrrolidone (PVP), which PVP has been rendered insoluble in water and body fluids by being complexed with a polyurethane, thus rendering the polyvinylpyrrolidone insoluble while still permitting the release of the anti-bacterial agent. The thus-formed material is useful per se to supply an anti-bacterial agent in the form of a pad (such as a foam pad), a bandage or the like or as a coating for a medical device such as a catheter. The material may be used as a foam, for example, between the toes in the treatment of athlete's foot (tinia pedis) which involves a fungal infection by trychophyton mentagrophytes.

Previously, iodine complexed with insoluble polyvinylpyrrolidone has been made by using special alkaline catalysts when polymerizing (see U.S. Pat. No. 3,136,755 to Grosser, et al. incorporated herein by reference) but these complexes are not useful for coating medical devices because the polymeric-iodine complexes are not soluble in any solvents. Furthermore, the Grosser, et al. polyvinylpyrrolidoneiodine complexes cannot be used as a coating since these complexes are insoluble, and the Grosser, et al. complexes do not form the useful sponge-like materials of this invention.

SUMMARY OF THE INVENTION

An anti-bacterial or bio-effecting medical material which may also have anti-fungal activity, comprises (1) a polyurethane complexed with polyvinylpyrrolidone, and (2) an anti-bacterial agent (which may also have anti-fungal activity) complexed with the polyvinylpyrrolidone. The material is used per se, such as in the form of a foam, and as a coating for medical devices such as, for example, catheters and wound drainage tubes.

In one embodiment of the invention, the material can be a foam prepared from polyurethane and polyvinylpyrrolidone to form a complex. A bio-effecting agent, such as an anti-bacterial or anti-fungal agent, etc. can be complexed with the polyvinylpyrrolidone. Further with regard to this embodiment, molecular iodine can be contacted with polyurethane-polyvinylpyrrolidone complex whereby at least some of the iodine forms a complex with the polyvinylpyrrolidone present in the polyurethane-polyvinylpyrrolidone foam complex. In related, commonly-owned U.S. Pat. No. 4,550,126 to Lorenz, a hydrophilic, flexible, open cell polyurethane polyvinylpyrrolidone interpolymer foam is disclosed which is formed by reacting under interpolymer and foam-forming conditions (a) a substantially linear isocyanate-capped polyether polyol prepolymer having an average reactive functionality of less than about 2.0 with (b) a poly(N-vinyl lactam) and (c) a foam forming amount of water in the presence of (d) a cell formation-regulating amount of surface active agent. The foam material of the present invention does not require the use of a linear isocyanate-capped polyether polyol prepolymer having an average functionality of less than about 2.0.

Another embodiment of the present invention is a coating material including a polyurethane complexed with a polyvinylpyrrolidone which can be contacted with a bio-effecting agent, such as an anti-bacterial agent, for complexing with the polyvinylpyrrolidone. As a result of this combination, the anti-bacterial agent can be slowly released in the presence of a fluid such as water and body fluids.

Examples of bio-effecting agents useful in the present invention can include, but are not limited to, anti-bacterial and anti-fungal agents, analgesics, antibiotics, anesthetics, odor-enhancers, adhesives, lubricants, etc. When the bio-effecting agent is contacted with the polyurethane-polyvinylpyrrolidone in a solution the agent can form a complex with the polyvinylpyrrolidone which is released slowly in water or body fluids.

Thus, the present invention provides a medical material, such as a foam or a film, which can be used for controlled release of a bio-effecting agent.

For a better understanding of the present invention, together with other and further objects, reference is made to the following description, taken in conjunction with the accompanying drawings, and its scope will be pointed out in the appended claims.

DETAILED DESCRIPTION OF THE INVENTION

Figure 1:
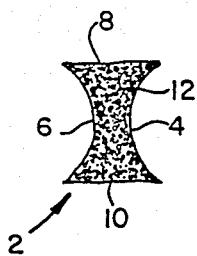
FIG. 1 is a front elevation of a device for treating athlete's foot.
Figure 2:
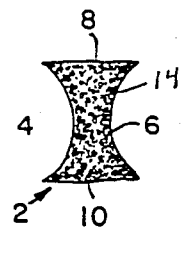
FIG. 2 is a rear elevation of the device of FIG. 1.
Figure 3:
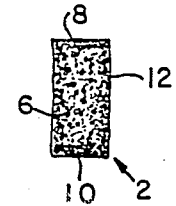
FIG. 3 is a right-side elevational view of the device of FIG. 1.
Figure 4:
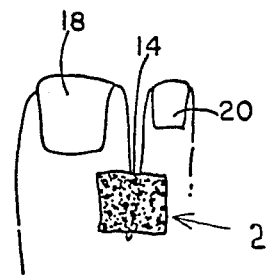
FIG. 4 is a plan view, partially broken away, showing the device of FIG. 1 between the toes.

The medical material in accordance with the invention comprises a polyurethane complexed with polyvinylpyrrolidone which in turn is complexed with a bio-effecting agent, such as an anti-bacterial agent which may also be an anti-fungal agent.

It is known to complex a polyurethane with polyvinylpyrrolidone. The exact nature of the complexing is not known, but the polyvinylpyrrolidone is, in any event, bound to the polyurethane in a form which is referred to in the art as a complex (some refer to this particular complex as an interpolymer). These complexes and the manner of making them are well-known to the art as seen, for example, in U.S. Pat. No. 4,100,309.

Typical polyvinylpyrrolidone-polyurethane complexes are polyvinylpyrrolidone complexed with polytetramethylene ether glycol-diphenylmethane diisocyanate (MDI), polytetramethylene ether glycol-tolylene diisocyanate (TDI), polytetramethylene ether glycol-isophorone diisocyanate, poly(1,4-oxybutylene) glycol-diphenylmethane diisocyanate (MDI), poly(1,4-oxybutylene) glycol-tolylene diisocyanate (TDI), poly(1,4-oxybutylene) glycol-isophorone diisocyanate, polyethylene glycol-diphenylmethane diisocyanate (MDI), polyethylene glycol-tolylene diisocyanate (TDI), polyethylene glycol-isophorone diisocyanate, polypropylene glycol-diphenylmethane diisocyanate (MDI), polypropylene glycol-tolylene diisocyanate (TDI), polypropylene glycol-isophorone diisocyanate, polycaprolactone-diphenylmethane diisocyanate (MDI), polycaprolactone-tolylene diisocyanate (TDI), polycaprolactone-isophorone diisocyanate, polyethylene adipate-diphenylmethane diisocyanate (MDI), polyethylene adipate-tolylene diisocyanate (TDI), polyethylene adipate-isophorone diisocyanate, polytetra-methylene adipate-diphenylmethane diisocyanate (MDI), polytetramethylene adipate-tolylene diisocyanate (TDI), polytetramethylene adipate-isophorone diisocyanate, polyethylene-propylene adipate-diphenylmethane diisocyanate (MDI), polyethylene-propylene adipate-tolylene diisocyanate (TDI), or polyethylene-propylene adipate-isophorone diisocyanate polyurethanes.

Preferred prepolymers for use in making the material of the invention are pentaerythritolethoxylatetoluene diisocyanate prepolymer and methylene bis phenylisocyanate (MDI)- rincinoleic acid glyceride prepolymer. Suitable polyurethane foam prepolymers are disclosed in U.S. Pat. Nos. 4,137,200 and 4,160,076. Reference may be had to Encyclopedia of Polymer Science and Technology, H. F. Mark, N. G. Gaylord, and N. M. Bikales (Eds. 1969), incorporated herein by reference, for further polyurethanes and prepolymers for making polyurethanes.

When the material of the invention is to be used per se as distinguished from being used as a coating on a substrate, it is preferred to use a resilient open-celled hydrophilic polyurethane foam. Advantageously the foam will have a density of from about 1.5 to about 15 lbs. Such polyurethane foams are well-known in the art. Exemplary are the above polyurethanes which are blown on being produced using water. Such polyurethane foams are disclosed in U.S. Pat. Nos. 4,160,076 and 4,137,200 which are incorporated herein by reference.

The material of the invention can be made either from pre-formed polyurethane which is then reacted with an isocyanate prepolymer and polyvinylpyrrolidone to bind the polyvinylpyrrolidone to the polyurethane or the polyvinylpyrrolidone can be mixed with an isocyanate prepolymer before it is used to form a polyurethane foam.

When the material of the invention is to be used as a coating on a substrate, a polyisocyanate prepolymer and polyvinylpyrrolidone are placed in a solvent and the thus-formed solution is applied to the substrate by dipping, spraying, brushing or the like. The ratio of the PVP to polyurethane in the coating (on a 100% wt. basis), can be from about 10:1 to about 1:1, and is preferably from about 7:1 to about 3:1. Typically, the thus-formed coating is air-dried and then cured at, for example, 60° C. for about 15 minutes. Typical substrates are polyurethanes, vinyl resins such as polyvinylchloride, polyacrylates such as polymethylmethacrylate, polycarbonates, polyesters such as polyethylene terephthalate, polybutylene terephthalate, polytetramethyl terephthalate or rubber such as latex rubber or polyisoprene.

Advantageously, the polyvinylpyrrolidone will have a K-value of at least 85. In the case of foam preparation, preferably the polyvinylpyrrolidone bound to the polyurethane will be from about 1% to about 20%, preferably from about 5% to about 15%, by weight of the combined weight of the polyurethane and the polyvinylpyrrolidone.

Various bio-effecting agents can be complexed to either foams or coatings of the polyvinylpyrrolidone-urethane complexes, such as potassium triiodide, miconazole, oxytetracycline, salicyclic acid, tolnaftate and benzocaine. The bio-effecting agents can be incorporated in varying ways depending on their reactivity with isocyanates. If they would react, then they must be incorporated after the foam or coating is produced by finding a solvent for the bio-effecting agent which is not a solvent for the PVP-urethane complex. If the bio-effecting agent is water soluble, for example, then complex with the PVP-urethane can be achieved by immersing the foam or coated object in the aqueous solution of the bio-effecting agent. If the bio-effecting agent is not reactive with isocyanates, it can be incorporated during the formation of the coating or foam. The bio-effecting agent, depending on the application, is generally present in an amount of from about 1% to about 20% by weight of the polyvinylpyrrolidone-urethane complex.

EXAMPLE 1

A slab of conventional resilient open-celled polyurethane (water-foamed polyethylene glycol-trimethylolpropane-toluene diisocyanate) of density of about 2 was dipped into a solution containing the following ingredients: 300 ml of methyl ethyl ketone, 100 ml of ethyl lactate, 9 gm of polyvinylpyrrolidone (K-90) and 2.25 gm of an isocyanate terminated prepolymer (methylenebis phenyl isocyanate (MDI) and ricinoleic acid glyceride). Excess solution was removed by running the foam through a squeezer roll. The foam was then air-dried for 30 minutes and finally heated in a forced draft oven at 60° C. for 1 hour. The foam was removed, cooled to room temperature and washed with water to remove any unreacted polyvinylpyrrolidone. Excess water was removed by again running the foam through a squeezer roll. The damp foam was then dipped into a 0.01 N potassium triiodide water solution for 1 minute. The excess solution was removed by running the foam through a squeezer roll and the foam was washed with water until no iodine color was observed in the wash water—about 2 washes. The foam was then dried in a forced draft oven at 60° C. for 3 hours. The available iodine in the foam was determined by taking a weighed sample of foam and adding it to a standard sodium thiosulfate solution and agitating for 24 hours and finally back titrating the solution with standard triiodide solution using a starch indicator solution. Under these conditions the foam contains approximately 6% available iodine.

Using standard microbiological tests, pieces of the foam showed significant zones of inhibition against staphylococcus aureus, candida albicans, and trichophyton mentagrophytes, using the spread plate method. Using the AOAC Method to determine sporocidal activity, kill was obtained at 10 minutes using a sample of the foam. Controls of the untreated foam itself and also the foam with bound polyvinylpyrrolidone without complexed iodine showed no activity.

EXAMPLE 2

A hydrophilic polyurethane foam bun was prepared in the following manner. Polyvinylpyrrolidone (K-90) 100 gms was dissolved in 900 gms of water to which was added 8.0 gm of a surface active agent having an HLB of 13.5 (Triton X-100) and 2.0 gm of a liquid defoaming agent having a HLB of 7 (Pluronic L-62 of BASF Wyandotte). The aqueous solution was mixed with 1000 gms of Hypol 2002 (an isocyanate terminated prepolymer made of toluene diisocyanate and an ethoxylated glycerine, see U.S. Pat. No. 4,160,076) and quickly poured into a pan. After the foam had risen it was allowed to stand for 3 days to finish curing. It was then sliced and pieces were punched out which were of a biconcave structure with anvil-shaped ends. They were washed with water to remove any unreacted polyvinylpyrrolidone and finally reacted with a potassium triiodide water solution (0.01 N) for 1 minute with agitation. The foam pieces were then washed with water to remove any excess triiodide not complexed to the polyvinylpyrrolidone and dried in an oven at 60° C. for 1 hour. The available iodine was determined as in Example 1 to be 5.5%.

Microbiological tests confirmed that the foam had killing power for *staphylococcus aureus, candida albicans* and *trichophyton mentagrophytes.*

EXAMPLE 3

A polyvinylchloride urethral catheter was coated by dipping in a solution comprised of methyl ethyl ketone and 25 ml of diacetone alcohol containing 2.50 gm of polyvinylpyrrolidone (K-90) and 1.25 gm of pentaerythritol ethyloxylate-toluene diisocyanate prepolymer (Hypol FHP3000 of W. R. Grace). The coating was air-dried for 5 minutes and cured at 60° C. for 15 minutes. The coated catheter was then wetted with water and then placed in a 0.01 N potassium triiodide solution for 1 minute. The coating immediately picked up the iodine color. After drying the iodine-containing coating and washing with fresh distilled water it was observed that the iodine color remained even on heating at 60° C. for 24 hours. Titration of the available iodine with sodium thiosulfate confirmed the presence of active iodine.

A 1 cm length of the coated catheter was left in contact with a growing *staphylococcus aureus* colony at 37° C. for 15 minutes and then an aliquot was put on a culture plate. No growth was observed; a control without contact has 910 counts and one with contact with a non-iodinated coated tube has 900 counts. A similar experiment using *candida albicans* again showed complete kill. Similar experiments of higher levels of available iodine showed it also killed trichophyton mentagrophytes.

EXAMPLE 4

The coating of a urethane tube is accomplished by dipping in a solution containing 300 ml of methyl ethyl ketone, 100 ml of ethyl lactate, 9 gm of polyvinylpyrrolidone (K-90) and 2.25 gm of isocyanate terminated ricinoleate prepolymer mixed with a chlorinated rubber as described in U.S. Pat. No. 4,217,254. After air drying for 5 minutes, the coating is cured at 60° C. for 1 hour. The coated tube is wetted with water and then dipped in 0.1N potassium triiodide solution for 30 seconds. The coating rapidly picks up the iodine color of the solution and retains it both on washing with water and on heating. The iodine content is titrable with sodium thiosulfate showing it has available iodine.

Similar experiments as in Example 3 shows it to be bactericidal, and that is kills fungi and yeasts.

EXAMPLE 5

A coating on a polyvinylchloride sheet was prepared, following the procedure of Example 4, but the wetted coating was placed in a 0.1% solution of hexachlorophene in water for 1 hour. The concentration of the hexachlorophene after being in contact was measured and it was found to have decreased due to the complexation with the coating.

The material of the invention can be used, for example, as a device for delivering an anti-bacterial agent and/or an anti-fungal agent to a body site. Advantageously the material will be in the form of a pad. It is preferred to have it in the form of a foam pad.

A typical device is a pad formed of a complexed polyurethane-polyvinylpyrrolidone with the polyvinylpyrrolidone complexed with an agent which has both anti-fungal and anti-bacterial activity for the treatment of athlete's foot. Advantageously the pad is made of a foam formed using a foamed polyurethane, for example, a hydrophilic foamed polyurethane formed from a cross-linked isocyanate-capped polyoxyethylene polyol prepolymer. Examples of suitable cross-linked foams are found in U.S. Pat. Nos. 4,137,200 and 4,160,076. The polyvinylpyrrolidone may be complexed with the foamed polyurethane either by mixing it with the prepolymer or after the polyurethane foam is formed as detailed above.

The work of Examples 1, 2, 3 and 5 was actually carried out.

EXAMPLE 6

A silicone Foley catheter was coated by dipping for 1 minute into a solution comprising 2100 ml of methyl ethyl ketone, 850 ml ethyl lactate, 300 ml cyclohexane in which is dissolved 58.5 gms polyvinyl-2-pyrrolidone (K-90) and 21.5 gms of a 60% solution in methyl ethyl ketone of an isocyanate terminated MDI-ricinoleate prepolymer mixed with a chlorinated rubber, as described in U.S. Pat. No. 4,217,254, incorporated herein by reference, air dried for 20 minutes, and finally heating at 60° C. for 15 minutes. After cooling to room temperature, the catheter was dipped into a 1% aqueous solution of Tetracycline hydrochloride for 10 minutes. A yellow color was observed to be picked up on the catheter. It was then dried in an oven at 60° C. for 10 minutes. Using zones of inhibition studies, it was found that it showed activity against both *staphylococcus aureus* and *E. Coli.*

EXAMPLE 7

A polyvinylidene chloride sheet was coated using a wire wound rod and a solution comprising 300 ml of methyl ethyl ketone, 100 ml of ethyl lactate, 9 gms of polyvinylpyrrolidone (K-90) and 2.25 gm of an isocyanate terminated ricinoleate prepolymer mixed with chlorinated rubber, as described in U.S. Pat. No. 4,217,254. After air drying for 10 minutes, the coating was cured at 60° C. for 30 minutes. The sheet, after cooling, was wetted with water and then dipped into an aqueous solution of salicyclic acid and agitated for 1 minute. It was washed with water and dried.

A piece of film, when placed in water, slowly releases salicyclic acid evidenced by titration with base of aliquots removed from the aqueous solution. A film of the coated material could be used in treatment of corns and calluses.

EXAMPLE 8

A coating solution consisting of 300 ml of methyl ethyl ketone, 100 ml of ethyl lactate, 9 gms of polyvinylpyrrolidone and 2.25 gms of an isocyanate terminated prepolymer of methylenediisocyanate reacted with a ricinoleate ester and mixed with chlorinated rubber, as described in U.S. Pat. No. 4,217,254, and containing 1.25 gm of benzocaine was coated on a polyester film. After air drying for 30 minutes, it was cured at 60° for 20 minutes.

A piece of the coated film was placed in water and samples removed periodically and analyzed for benzocaine. Results indicated slow release of the benzocaine over a 24 hour period. Such a film could be useful in the treatment of mouth canker sores.

EXAMPLE 9

A woven polyester mat was coated by dipping into a solution as in Example 7 and cured in the same manner. A solution of billirubin in a buffered saline solution was prepared to simulate its presence in blood. The coated polyester was placed in contact with the billirubin solution and samples removed from the solution showed that 338 mg of billirubin were removed per gm of the coating. Thus suggests that a coated polyester might be useful in removing this waste product in blood dialysis equipment.

EXAMPLE 10

A coating solution comprising 300 ml of methyl ethyl ketone, 100 ml ethyl lactate, 9 gm of polyvinylpyrrolidone, 0.34 gm of chlorohexidene acetate and 3 gm of an MDI-ricinoleate ester with chlorinated rubber was sprayed on a polyester film using a compressed air spray gun. It was cured after air drying for 5 minutes at 60° C. for 15 minutes.

If the film was hydrated by a humidity greater than 75%, then bacteria placed on its surface was killed. If the humidity was low, it did not function to kill bacteria. If the film was placed on an agar plate containing bacteria, it killed the bacteria.

By the actual examples disclosed above, it has been shown that a variety of drugs can be complexed to the coating of the invention and the different areas in which the application may be useful. Other bio-effecting agents, in addition to the examples that have been tried and shown to be incorporated in complexes include Retinoic Acid, Miconazole, Griseofulvin, Ascorbic Acid, 4-Chloro-3,5-Dimethyl Phenol, Ampicillin, Cephalosporcin C, Methicillin, Amphotericin, Lidocaine, and Resorcinol. Perfumes and indicator dyes could also be complexed in the coatings.

Some preferred agents are iodine, potassium triiodide, miconazole nitrate, tolnaftate, benzocaine, salicyclic acid as detailed above.

In the case of a foam for use in treating athlete's foot, a pad will be sized to fit between two toes and have a height about equal to the thickness (depth) of the toes. The sides of the pad are preferably concave to accommodate the toes.

Referring to FIG. 1, a polyurethane sponge 2 has concave sides 4 and 6, a flat top 8 and a flat bottom 10. It also has a substantially flat front 12 and a substantially flat rear 14. The concave sides 4 and 6 provide for a comfortable fit of the sponge 2 between a pair of toes such as a big toe 18 and an adjacent toe 20. The concave sides 4 and 6 also assist in retaining the sponge 2 between said toes.

Sponge 2 may be formed of the material made in example 2, thus providing for the gradual release of iodine for the treatment of athlete's foot on toes 18 and 20.

Figure 5:
FIG. 5 is a plan view, partially broken away, of a peristaltic pump tube.

Referring now to FIG. 5, a peristaltic pump tube 30 of polyvinylchloride has a coating 32 of a complexed polyurethane-polyvinylpyrrolidone having the polyvinylpyrrolidone complexed with potassium triiodide. This tube can be formed following the general procedure outlined in example 3.

Figure 6:
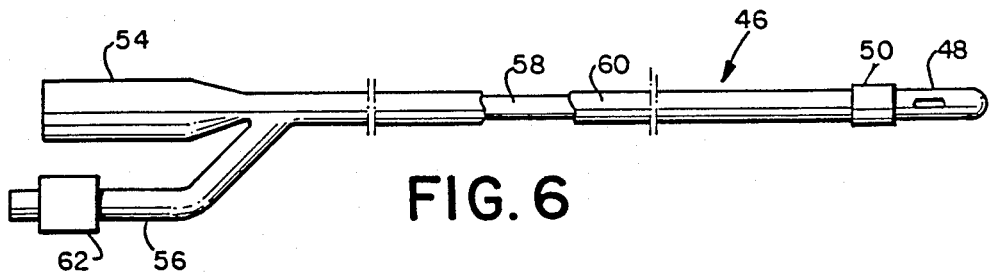
FIG. 6 is a plan view of a urethral catheter, partially broken away.

Referring to FIG. 6, a urethral catheter 46 has a tip 48, a balloon portion 50, a drain connector 54 and a valve branch 56 formed from a branched tube 58 of rubber latex coated with cross-linked polyurethane-polyvinylpyrrolidone with the polyvinylpyrrolidone complexed with hexachlorophene.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:
1. A medical material comprising:
   an anti-bacterial agent or anti-fungal agent complexed with polyvinylpyrrolidone which has been rendered insoluble in water and body fluids by being complexed with a polyurethane prior to complexing with said agent; said medical material being capable of releasing said anti-bacterial- or anti-fungal-polyvinylpyrrolidone complexed agent from said polyurethane-polyvinylpyrrolidone com- plex when said complex is in contact with water or body fluids.

2. An anti-bacterial medical material in accordance with claim 1 in which the anti-bacterial agent is iodine, an iodide, hexachlorophene, griseofulvin, or miconazole nitrate.

3. A material in accordance with claim 1 in which the polyurethane is foamed.

4. An anti-bacterial article comprising:
a substrate,
a coating on the substrate comprising a polyurethane complexed with polyvinylpyrrolidone and an anti-bacterial agent complexed with said polyvinylpyrrolidone.

5. An anti-bacterial article in accordance with claim 4 in which the substrate is selected from the group consisting of polyurethane, a vinyl resin, a polyacrylate, a polycarbonate, a polyester or rubber.

6. A device for treating athlete's foot comprising a pad of a polyurethane foam complexed with polyvinylpyrrolidone which is complexed with an anti-bacterial and anti-fungal agent.

7. The device of claim 6 in which the agent is iodine.

8. The device of claim 6 in which the agent is an iodide.

9. The device of claim 6 in which the agent is selected from the group consisting of halides, halogens, hexachlorophene, griseofulvin, and miconazole nitrate.

10. The device of any of claims 6 through 9 in which the pad has opposed concave sides for the reception of toes.

11. A medical material obtained from the process which comprises contacting a polyurethane-polyvinylpyrrolidone foam complex with a bio-effecting agent whereby at least some of the bio-effecting agent forms a complex with the polyvinylpyrrolidone present in the polyurethane-polyvinylpyrrolidone foam complex, said medical material releasing water-soluble polyvinylpyrrolidone-bio-effecting complex when contacted with water or a body fluid.

12. The medical material of claim 11 wherein said bio-effecting agent is selected from the group consisting of anti-bacterial agents, anti-fungal agents, analgesics, antibiotics, anesthetics, odor-enhancers, dyes, adhesives, and lubricants.

13. The medical material of claim 12 wherein said agent is selected from the group consisting of iodine, iodide, hexachlorophene, griseofulvin, miconazole nitrate, tolnaftate, benzocaine, salicyclic acid, retinoic acid, ascorbic acid, 4-chloro-3,5-dimethyl phenol, ampicillin, cephalosporcin C, methicillin, amphotericin, lidocaine, and resorcinol.

14. The medical material of claim 13 wherein said bio-effecting agent is iodine.

15. A medical material obtained from the process which comprises contacting a polyurethane-polyvinylpyrrolidone film complex with a bio-effecting agent whereby at least some of the bio-effecting agent forms a complex with the polyvinylpyrrolidone present in the polyurethane-polyvinylpyrrolidone film complex, said medical material releasing water-soluble polyvinylpyrrolidone-bio-effecting complex when contacted with water or a body fluid.

16. The medical material of claim 15 wherein said bio-effecting agent is selected from the group consisting of anti-bacterial agents, anti-fungal agents, analgesics, antibiotics, anesthetics, odor-enhancers, dyes, adhesives, and lubricants.

17. The medical material of claim 16 wherein said agent is selected from the group consisting of iodine, iodide, hexachlorophene, griseofulvin, miconazole nitrate, retinoic acid, ascorbic acid, 4-chloro-3,5-dimethyl phenol, ampicillin, cephalosporcin C, methicillin, amphotericin, lidocaine, and resorcinol.

18. The medical material of claim 17 wherein said bio-effecting agent is iodine.

* * * * *